(12) United States Patent
Cheng et al.

(10) Patent No.: US 9,087,742 B2
(45) Date of Patent: Jul. 21, 2015

(54) HIGH DENSITY MULTI-ELECTRODE ARRAY

(71) Applicant: International Business Machines Corporation, Armonk, NY (US)

(72) Inventors: Kangguo Cheng, Schenectady, NY (US); Arjang Hassibi, Austin, TX (US); Ali Khakifirooz, Mountain View, CA (US); Dharmendra S. Modha, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/798,446

(22) Filed: Mar. 13, 2013

(65) Prior Publication Data

US 2013/0187253 A1 Jul. 25, 2013

Related U.S. Application Data

(62) Division of application No. 13/307,608, filed on Nov. 30, 2011, now abandoned.

(51) Int. Cl.
*H01L 27/12* (2006.01)
*A61B 5/04* (2006.01)
*H01L 21/768* (2006.01)

(52) U.S. Cl.
CPC ........ *H01L 27/1203* (2013.01); *A61B 5/04001* (2013.01); *H01L 21/76898* (2013.01); *A61B 2562/028* (2013.01); *A61B 2562/046* (2013.01)

(58) Field of Classification Search
CPC ............... H01L 21/76898; H01L 27/1203
USPC ........ 600/116, 377, 378; 438/14, 48–49, 666; 257/506, 448, 737, 784, E23.021, 257/E21.158, E27.11
See application file for complete search history.

(56) References Cited

U.S. PATENT DOCUMENTS 4,969,468 A    11/1990   Byers et al.
5,215,088 A *   6/1993   Normann et al. ............. 600/377

(Continued)

FOREIGN PATENT DOCUMENTS

CN    101199042 A    6/2008
CN    102017070 A    4/2011

(Continued)

OTHER PUBLICATIONS

Bakkum et al., "Novel Neuronal Cellular and Network Measurements Enabled by a High-Density 11, 011-Microlectrode CMOS Array," Active Arrays and Electronics, 7th International Meeting on Substrate-Integrated Microelectrode Arrays, pp. 324-326, 2010.

(Continued)

*Primary Examiner* — Mamadou Diallo
*Assistant Examiner* — Christina Sylvia
(74) *Attorney, Agent, or Firm* — Cantor Colburn LLP; Libby Toub

(57) ABSTRACT

A high density micro-electrode array includes a transistor layer including a plurality of access transistors and a substrate in operable communication with the transistor layer including, wherein at least a portion of the substrate includes a plurality of trenches. The system includes a plurality of electrodes at least partially located in the plurality of trenches, wherein each of the plurality of electrodes is connected to at least one of the plurality of access transistors and wherein each of the electrodes is separated by a distance less than approximately one microns.

8 Claims, 11 Drawing Sheets

(56) References Cited

U.S. PATENT DOCUMENTS

| | | | |
|---|---|---|---|
| 6,087,197 | A | 7/2000 | Eriguchi et al. |
| 6,551,849 | B1 * | 4/2003 | Kenney ............ 438/34 |
| 7,127,301 | B1 | 10/2006 | Okandan et al. |
| 7,941,202 | B2 | 5/2011 | Hetke et al. |
| 2005/0113895 | A1 | 5/2005 | Danzl et al. |
| 2006/0276866 | A1 | 12/2006 | McCreery |
| 2007/0001173 | A1 * | 1/2007 | Brask et al. ............ 257/67 |
| 2009/0301994 | A1 | 12/2009 | Bhandari et al. |
| 2010/0145422 | A1 | 6/2010 | Seymour et al. |
| 2010/0168830 | A1 | 7/2010 | Hung et al. |
| 2010/0178810 | A2 | 7/2010 | Aarts et al. |
| 2010/0267186 | A1 | 10/2010 | Wang et al. |
| 2011/0014775 | A1 | 1/2011 | Akiyama et al. |
| 2011/0024771 | A1 | 2/2011 | Hajj-Hassan et al. |
| 2011/0054583 | A1 | 3/2011 | Litt et al. |
| 2011/0093052 | A1 | 4/2011 | Anderson et al. |
| 2011/0169065 | A1 | 7/2011 | Cheng et al. |
| 2011/0175152 | A1 | 7/2011 | Booth, Jr. et al. |

FOREIGN PATENT DOCUMENTS

| | | |
|---|---|---|
| WO | 2007139511 A1 | 12/2007 |
| WO | 2010079875 A1 | 7/2010 |

OTHER PUBLICATIONS

Bai et al., "A High-Yield Microassembly Structure for Three-Dimensional Microelectrode Arrays," IEEE Transactions on Biomedical Engineering, vol. 47, No. 3, pp. 281-289, Mar. 2000.

Bakkum et al., "Novel Neuronal Cellular and Network Measurements Enabled by a High-Density 11, 011-Microelectrode CMOS Array," Active Arrays and Eletronics, 7th International Meeting on Substrate-Integrated Microelectrodes Arrays, pp. 324-326.

International Search Report and Written Opinion of the International Searching Authority. PCT/US2012/067169; International Filing Date: Nov. 30, 2012; Mailing date: Mar. 13, 2013; 10 pages.

Wise et al., "Microelectrodes, Microelectronics, and Implantable Neural Microsystems," Proceedings of the IEEE, vol. 96, No. 7, pp. 1184-1202, Jul. 2008.

Hottowy et al., "512-electrode MEA System for Spatio-Temporal Distributed Stimulation and Recording of Neural Activity," Active Arrays and Electronics, 7th International Meeting on Substrate-Integrated Microelectrode Arrays, pp. 327-330, 2010.

Qing Bai et al., "A High-Yield Microassembly Structure for Three-Dimensional Microelectrode Arrays," IEEE Transactions on Biomedical Engineering, vol. 47, No. 3, pp. 281-289, Mar. 2000.

* cited by examiner

HIGH DENSITY MULTI-ELECTRODE ARRAY

CROSS REFERENCE TO RELATED APPLICATIONS

This application is a divisional of U.S. Non-Provisional application Ser. No. 13/307,608, which was filed on Nov. 30, 2011, the entirety of which is hereby incorporated by reference.

BACKGROUND

The present invention relates to multi-electrode arrays, and more specifically, to high density multi-electrode arrays.

Multi-electrode arrays are used for various applications including, for example, electrical interfacing to neurons. Multi-electrode arrays have been fabricated by a variety of methods and can be used for both in vivo or in vitro applications. Multi-electrode arrays can be used to stimulate or probe brain activity, to stimulate neurons and study the resulting neuron plasticity or to train live neural networks and use them for computation.

In currently available micro-electrode arrays, the density of the electrodes range from approximately one hundred electrodes per square millimeter in microelectromechanical systems (MEMS) arrays to approximately ten thousand electrodes per square millimeter in micro-fabricated arrays. These electrode densities are achieved using standard CMOS metallization techniques. The density of typical micro-electrode arrays is much smaller than typical neuron density. For example, the neuron density for visual cortex is approximately two hundred million neurons per cubic millimeter.

BRIEF SUMMARY

According to one embodiment of the present disclosure, a high density micro-electrode array includes a transistor layer including a plurality of access transistors and a substrate in operable communication with the transistor layer including, wherein at least a portion of the substrate includes a plurality of trenches. The system includes a plurality of electrodes at least partially located in the plurality of trenches, wherein each of the plurality of electrodes is connected to at least one of the plurality of access transistors and wherein each of the electrodes is separated by a distance less than approximately one microns.

According to another embodiment of the present disclosure, a high density micro-electrode array includes a transistor layer including a plurality of access transistors, wherein one or more of the plurality of access transistors is in operable communication with a stimulation circuit and wherein one or more of the plurality of access transistors is in operable communication with a detection circuit. The high density micro-electrode array includes a buried oxide layer formed on a portion of the transistor layer and a plurality of electrodes formed beneath the transistor layer, wherein each of the plurality of electrodes is connected to at least one of the plurality of access transistors and wherein the electrodes are separated by approximately one micron.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification.

The forgoing and other features, and advantages of the invention are apparent from the following detailed description taken in conjunction with the accompanying drawings in which:

FIGS. 1 through 4 are a series of cross sectional views illustrating a method of forming an exemplary high density micro-electrode array, in accordance with an exemplary embodiment, in which:

FIG. 1 illustrates a high density micro-electrode array having a plurality of tightly packed electrodes that are formed inside trenches in a substrate;

FIG. 2 illustrates thinning of a portion of the substrate of FIG. 1;

FIG. 3 illustrates etching of a portion of the dielectric liner from the tip of the electrodes in FIG. 2; and FIG. 4 illustrates forming an optional dielectric layer to insulate the remaining portion of the substrate in FIG. 3.

FIGS. 5, 6a and 6b are cross sectional views illustrating a method of forming an exemplary high density micro-electrode array, in accordance with an exemplary embodiment, in which:

FIG. 5 illustrates a high density multi-electrode array including a silicon-on-insulator (SOI) wafer that is used in the transistor layer above a buried oxide (BOX) layer;

FIG. 6a illustrates thinning of a portion of the substrate of FIG. 5;

FIG. 6b illustrates an alternative embodiment of the processing operation of FIG. 6a, in which the etching of the substrate continues all the way to the BOX layer;

DETAILED DESCRIPTION

Figure 1:
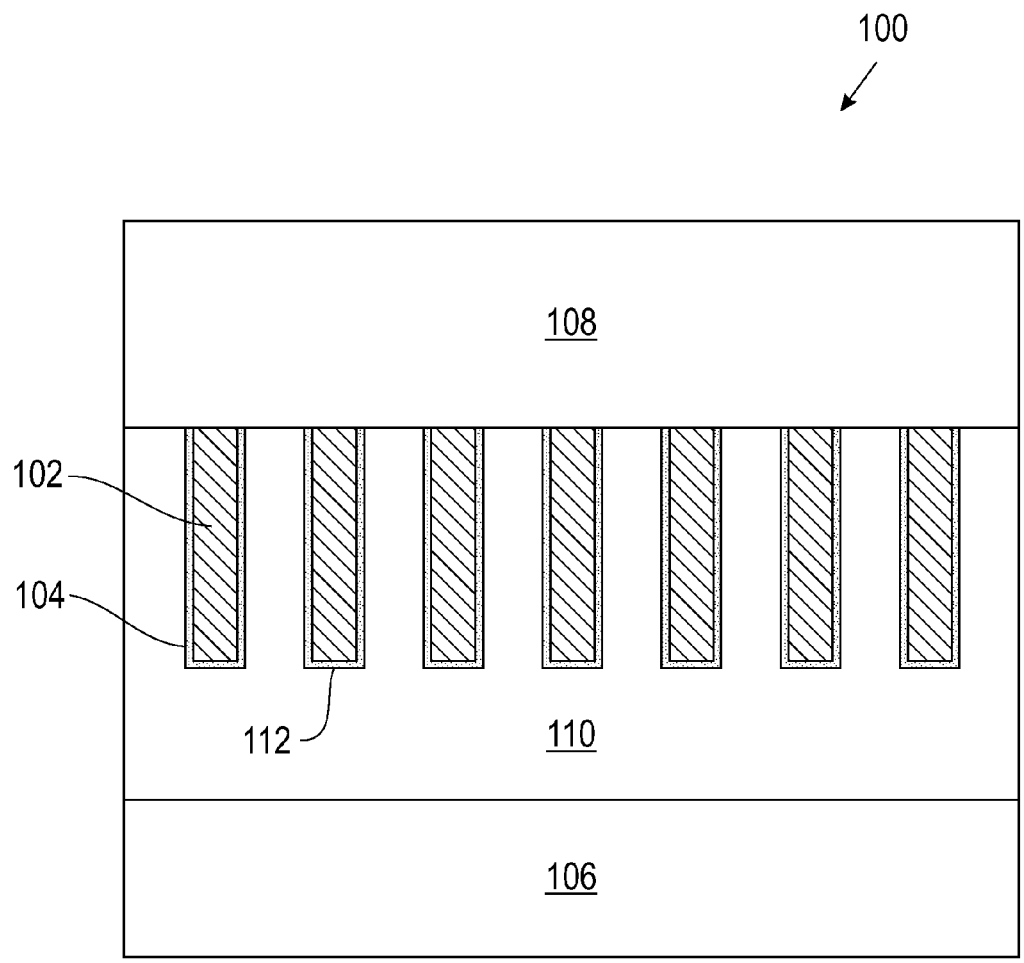

Embodiments of the disclosure are described herein with reference to cross-section illustrations that are schematic illustrations of idealized embodiments (and intermediate structures) of the invention. The thickness of layers and regions in the drawings may be exaggerated for clarity. Additionally, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of the disclosure.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

With reference now to FIG. 1, a cross section of a high density micro-electrode array 100 in accordance with an exemplary embodiment of the disclosure is shown. The high density micro-electrode array 100 includes a plurality of tightly packed electrodes 102 that are formed inside trenches 104 in the substrate 106. In exemplary embodiments, each electrode 102 is connected to at least one access transistor in the transistor layer 108 to enable addressing of each of individual electrodes 102.

In exemplary embodiments, the high density micro-electrode array 100 may be fabricated using a variety of techniques. In one exemplary embodiment, a high density micro-electrode array 100 is fabricated by starting with a substrate 106 that contains a heavily doped region 110 at the top of the substrate. In exemplary embodiments, the heavily doped region may only be few microns in thickness. The fabrication process includes forming trenches 104 in the heavily doped region 110 of the substrate 106 and filling the trenches 104 with a dielectric liner 112 and a conductive electrode 102. In one exemplary embodiment, the conductive electrode 102 may be a heavily doped polysilicon, as done for example in trench dynamic random access (DRAM) technology. In another exemplary embodiment, the conductive electrode 102 may contain a bio-compatible metal such as titanium or platinum. After the trenches 104 are lined and filled, each electrode 102 is connected to at least one access transistor (not specifically shown) in the transistor layer 108 for addressing thereof. In one embodiment, after formation of the electrodes 102 in the trenches 104, an access transistor and periphery circuits for sensing neuron activity and for stimulating are fabricated using standard CMOS processing. The periphery circuit may contain one or more of the following units: electrode addressing control, signal amplification and detection, neuron stimulation generation, timing, interface to outside chips/instrumentations, etc. After the electrodes 102 are connected to an access transistor in the transistor layer 108, the opposite side of the substrate 106 is thinned, exposing at least a portion of the electrodes 102. In exemplary embodiments, only a portion of the substrate 106 that contains the high density electrode array is thinned.

Figure 2:
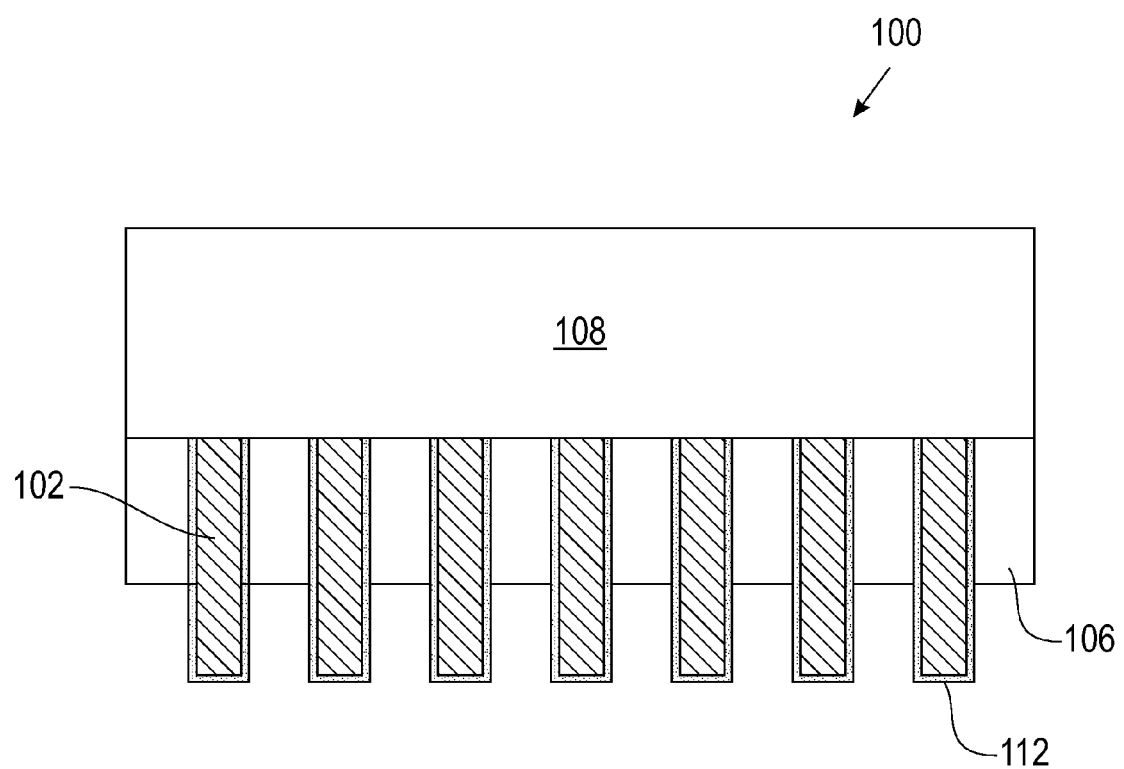

As then shown in FIG. 2, the substrate 106 has been thinned to a depth sufficient to expose at least a portion of the dielectric liner 112. The process of thinning the substrate 106 can be done by wafer thinning, grinding, etching, or other commonly known techniques. In exemplary embodiments, the substrate thinning process may include using wet/dry etching with good selectivity between the substrate 106 and the dielectric liner 112. For example, wet etching may be done using tetramethylammonium hydroxide (TMAH) or potassium hydroxide (KOH) to remove a portion of the substrate 106 and leave the dielectric liner 112 intact. Alternatively, dry etching based on hydrogen bromide (HBr) chemistry can be used which has good selectivity to the dielectric liner 112.

Figure 3:
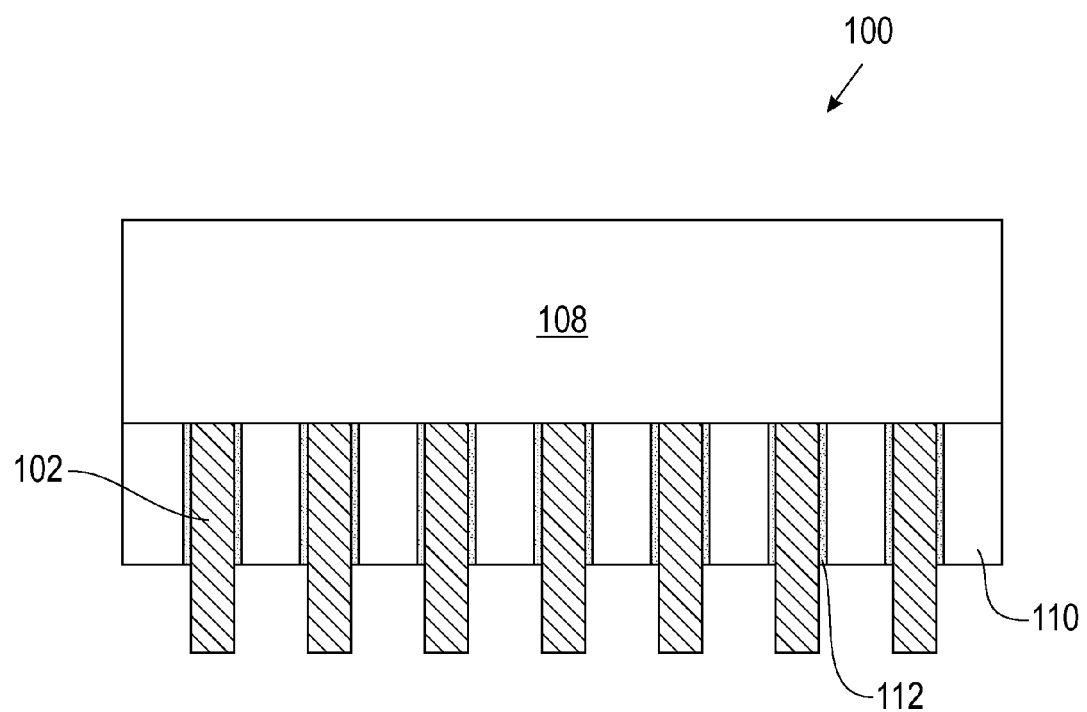
Figure 4:
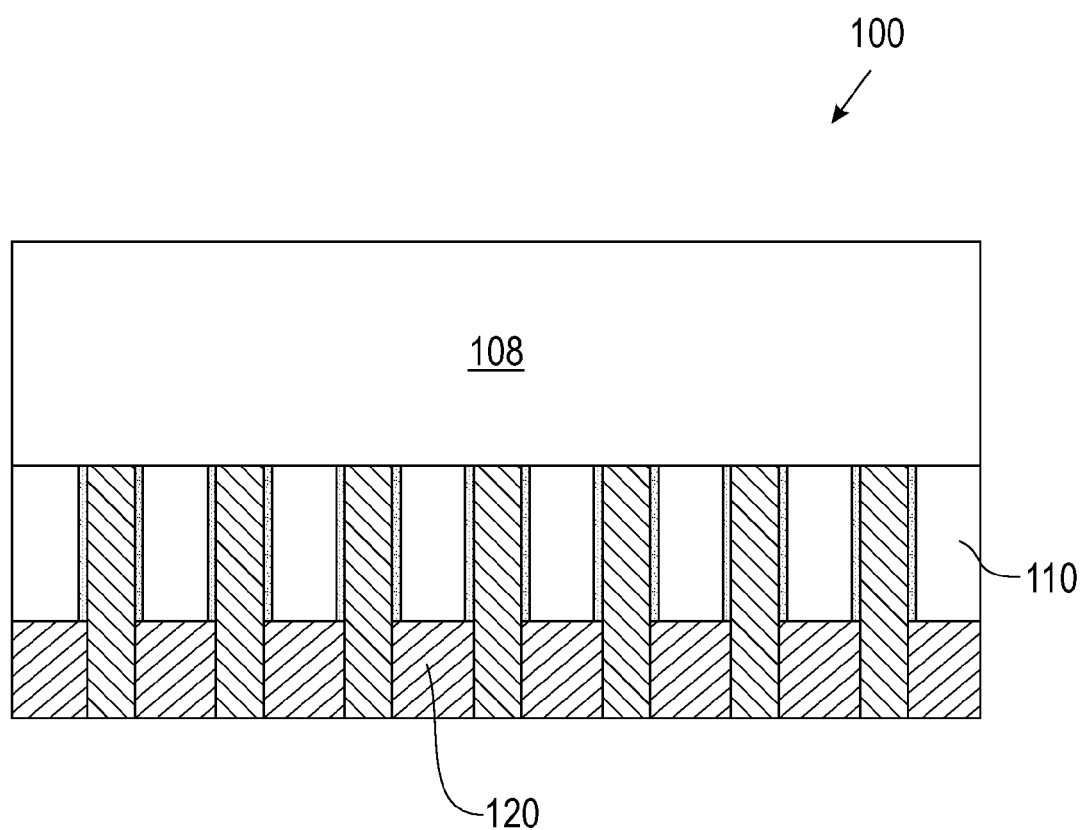

Continuing now with reference to FIG. 3, a portion of the dielectric liner 112 has been etched away from the tip of the electrodes 102, exposing the electrodes 102. As illustrated in FIG. 4, a dielectric layer 120 may optionally be used to insulate the remaining heavily doped region 110 of the substrate. In exemplary embodiments, the dielectric layer 120 may a polymer such as polymethylmethacrilate (PMMA), a spin-on-glass or another suitable alternative.

Figure 5:
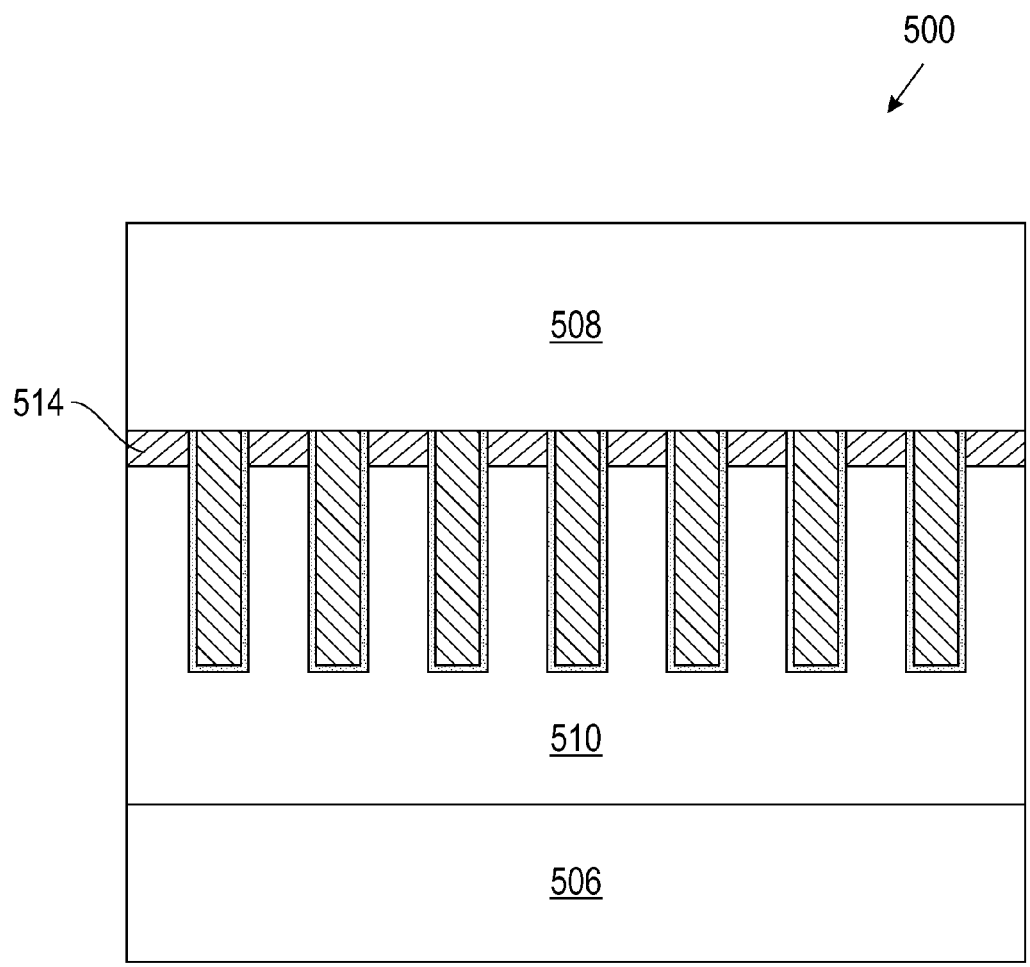
Figure 6A:
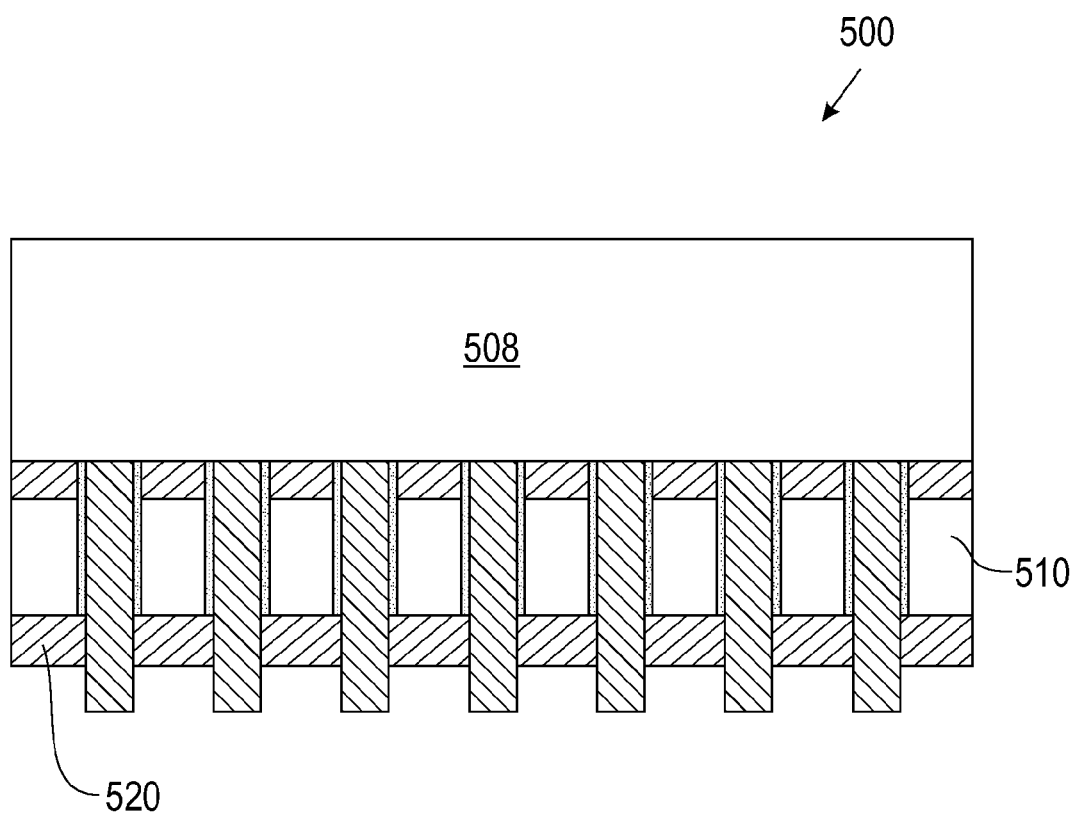
Figure 6B:
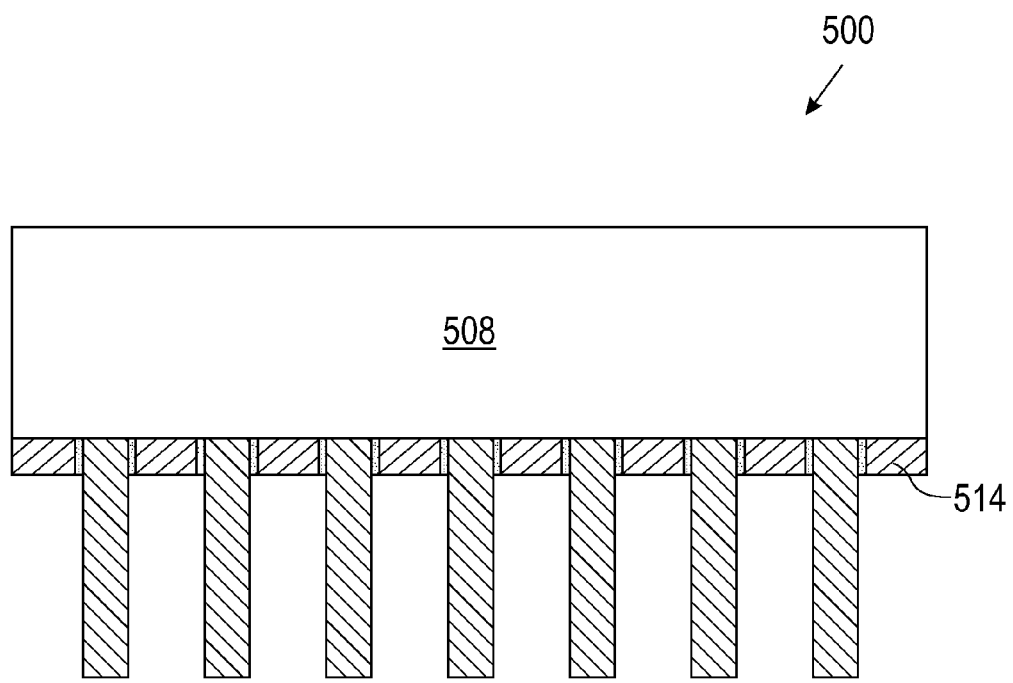

Turning now to FIG. 5, another exemplary embodiment of a high density multi-electrode array 500 is illustrated. The high density multi-electrode array 500 includes a silicon-on-insulator (SOI) wafer that is used in the transistor layer 508 above a buried oxide layer (BOX) 514. In one exemplary embodiment, as illustrated in FIG. 6a, during the fabrication of the high density multi-electrode array 500 a portion of the heavily doped region 510 of the substrate can be etched to a desired depth. Alternatively, as shown in FIG. 6b, the substrate may be etched down to the BOX 514.

Figure 7:
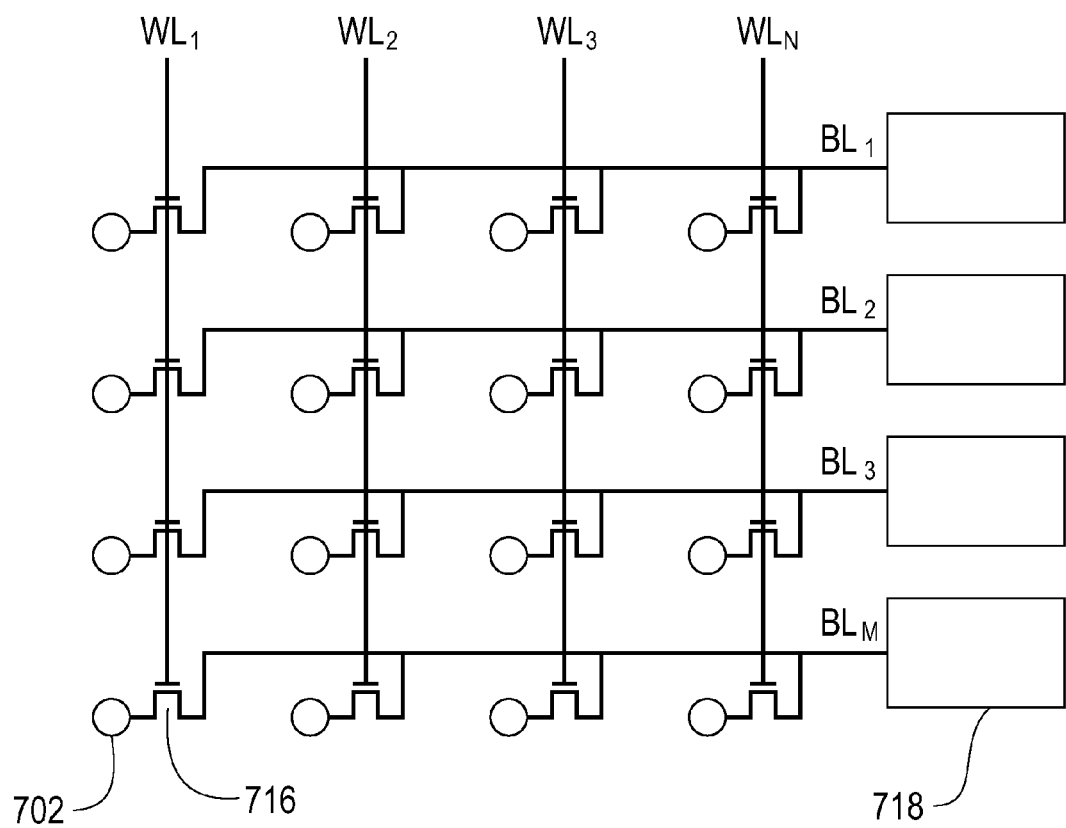
FIG. 7 is a circuit diagram of an exemplary addressing scheme for addressing electrodes in a high density multi-electrode array, in accordance with additional embodiments.

Referring now to FIG. 7, a circuit diagram of an exemplary addressing scheme for addressing electrodes in a high density multi-electrode array is shown. As illustrated, the electrodes 702 in the high density multi-electrode array can be addressed using a single access transistor 716 per electrode in a word line/bit line addressing scheme. The access transistors 716 connect the electrodes 702 to circuitry 718 which may be used to send or receive signals to or from the electrodes 702. In other exemplary embodiments, alternative configurations that use one or more transistors for addressing each electrode can be used. For example, in one embodiment two access transistors may be used to activate a single electrode with one access transistor being used for measuring neuron activity and another access transistor being used for stimulating neuron activity. In an alternative embodiment, some electrodes can be used exclusively for probing or measuring neuron activity while others are used exclusively for stimulating neuron activity.

Figure 8A:
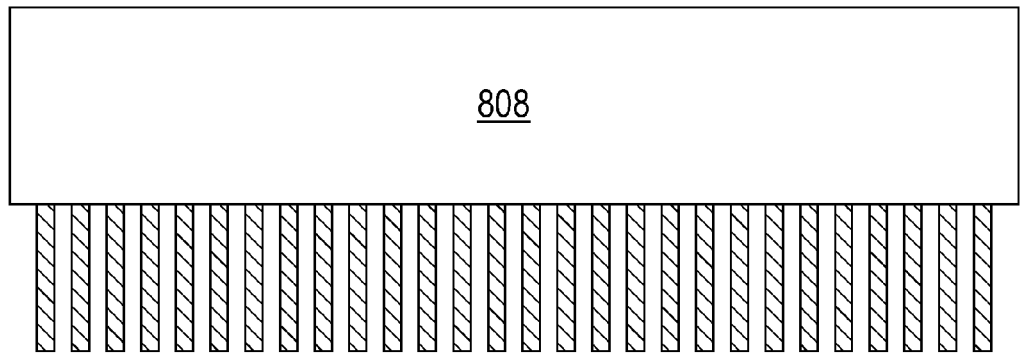
FIGS. 8a and 8b are cross sectional views of exemplary high density micro-electrode arrays, in accordance with additional embodiments.
Figure 8B:
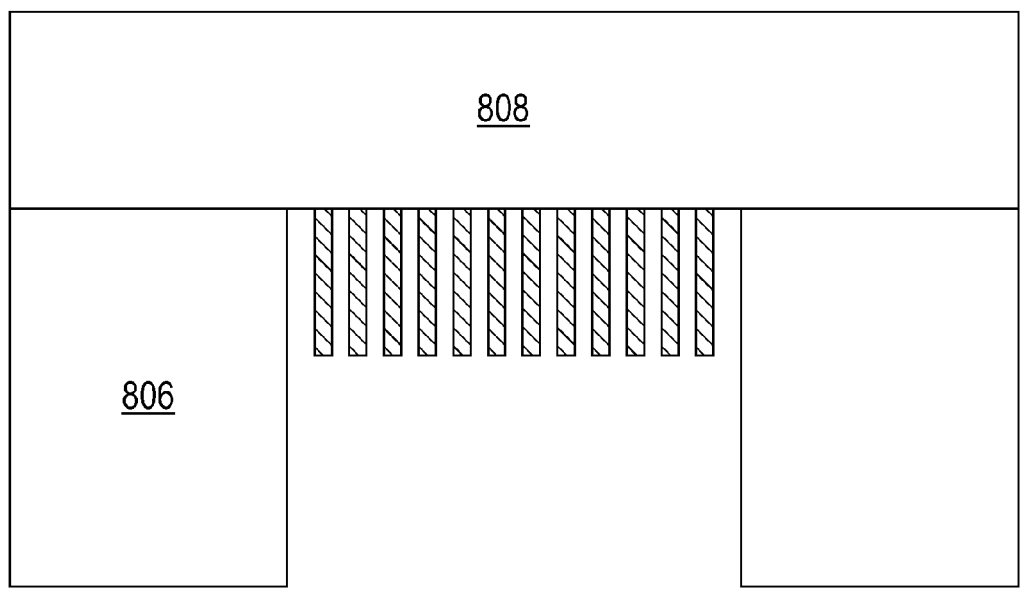

In exemplary embodiments, the high density multi-electrode array may be fabricated such that the high density multi-electrode array encompasses the entire substrate 806 or such that only a portion of the substrate is used for the high density multi-electrode, as illustrated respectively by FIGS. 8a and 8b. In the embodiment shown in FIG. 8b, only the portion of the substrate that contains the high density multi-electrode array is thinned during the fabrication process.

Figure 9:
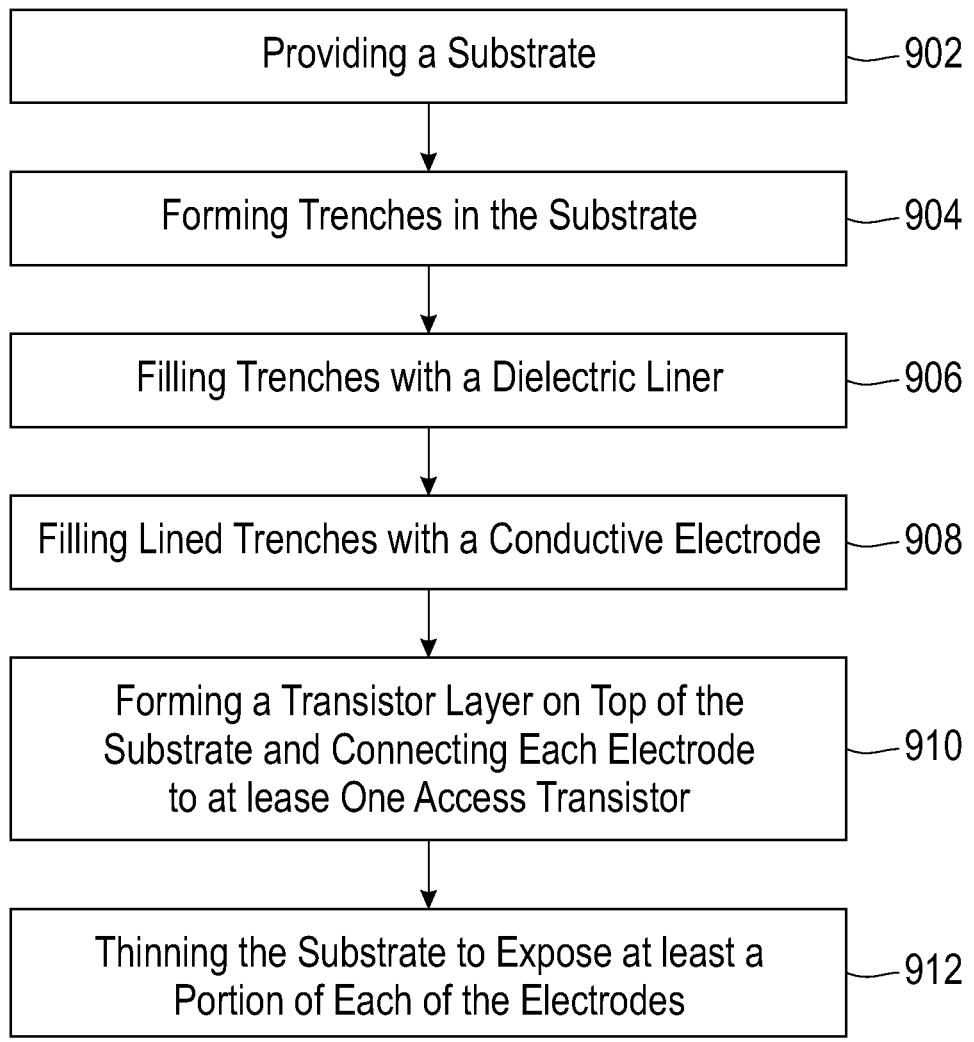
FIG. 9 is a flow diagram of an exemplary process for fabricating a high density micro-electrode array, in accordance with another embodiment.

Referring now to FIG. 9, a flow diagram illustrating an exemplary process for fabricating a high density micro-electrode array is illustrated. The first step in the exemplary fabrication process, as shown at process step 902, is providing a substrate that optionally contains a heavily doped region. After the substrate has been provided, the next step in the exemplary fabrication process is forming trenches in the substrate, as shown at process step 904. Once the trenches have been formed, they are filled with a dielectric liner and then a conductive electrode, as shown is process steps 906 and 908 respectively. The next step in the exemplary fabrication process, as illustrated at process step 910, is forming a transistor layer on top of the substrate and connecting each electrode to at least one access transistor. After the electrodes are connected to access transistors, the substrate is thinned to expose at least a portion of each of the electrodes, as shown at process step 912.

In exemplary embodiments, the process for fabricating a high density micro-electrode array may include an additional step of adding a dielectric layer to insulate the remaining portion of the substrate that surrounds the electrodes. The flow diagram depicting the process for fabricating a high density micro-electrode array is provided as just one exemplary fabrication process that can be used. There may be many variations to the fabrication process or the process steps described therein without departing from the spirit of the invention. For instance, the steps may be performed in a differing order or steps may be added, deleted or modified. All of these variations are considered a part of the claimed invention.

Figure 10:
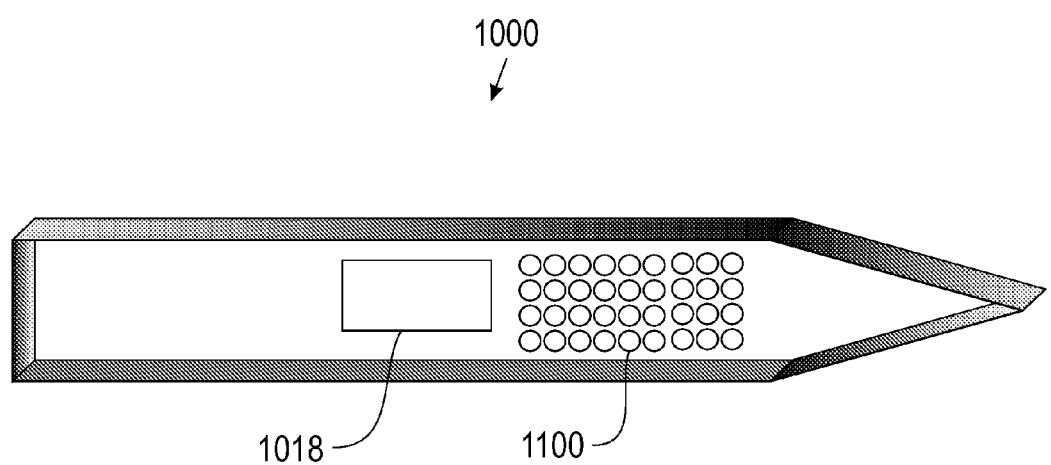
FIG. 10 is a perspective view of a micro-needle including a high density micro-electrode, in accordance with another embodiment.

Turning now to FIG. 10, a micro-needle 1000 suitable for in vivo applications that includes an exemplary embodiment of a high density micro-electrode array is illustrated. The micro needle 1000 includes layers of wafer each containing a high density micro-electrode array 1100 and periphery circuit 1018. The layers of wafer that make up the micro-needle 1000 are cut so that the dimensions and shape are suitable for in vivo applications. Typical micro-needles have a width and thickness of 20-50 μm and length of 100-1000 μm and contain about $10^3$ micro-electrodes on its side. In certain applications the micro-needles can be arranged in a one-dimensional or two-dimensional array as known in the art.

In exemplary embodiments a high density micro-electrode array in accordance with the present disclosure may have an electrode density of greater than approximately one hundred thousand electrodes per square millimeter. In other exemplary embodiments a high density micro-electrode array in accordance with the present invention may have an electrode density of greater than approximately one million electrodes per square millimeter. In exemplary embodiments, the electrodes in the high density micro-electrode are formed such that the distance separating the electrodes can range from approximately two hundred nanometers (nm) to approximately two microns (μm).

The method as described above is used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A system comprising:
   a transistor layer comprising a plurality of access transistors;
   a substrate in operable communication with the transistor layer, wherein at least a portion of substrate includes a plurality of trenches;
   a plurality of electrodes at least partially located in the plurality of trenches, wherein each of the plurality of electrodes is connected to at least one of the plurality of access transistors and wherein each of the electrodes is separated by a distance less than approximately one microns;
   a dielectric liner disposed on a first portion of a sidewall of each of the plurality of electrodes adjacent to the substrate; and
   a dielectric layer formed on the substrate between second portions of adjacent electrodes, wherein the dielectric layer is deposited on the surface of the substrate and on the surface of the dielectric liner, wherein a surface portion of each of the plurality of electrodes is coplanar with a surface portion of the dielectric layer.

2. The system of claim 1, further comprising a buried oxide layer disposed between the transistor layer and the substrate.

3. The system of claim 1, wherein the transistor layer comprises a silicon-on-insulator layer.

4. The system of claim 1, wherein one or more of the plurality of access transistors are in operable communication with a stimulation circuit.

5. The system of claim 1, wherein each of the plurality of access transistors are in operable communication with a stimulation circuit and a detection circuit.

6. A system comprising:
   a transistor layer comprising a plurality of access transistors, wherein one or more of the plurality of access transistors is in operable communication with a stimulation circuit and wherein one or more of the plurality of access transistors is in operable communication with a detection circuit;
   a buried oxide layer formed on a portion of the transistor layer;
   a plurality of electrodes formed beneath the transistor layer, wherein each of the plurality of electrodes is connected to at least one of the plurality of access transistors, and wherein the electrodes are separated by approximately one micron;

a dielectric liner disposed on a first portion of a sidewall of each of the plurality of electrodes adjacent to a substrate disposed between adjacent electrodes; and a dielectric layer formed on the substrate between second portions of adjacent electrodes, wherein the dielectric layer is deposited on the surface of the substrate and on the surface of the dielectric liner, wherein a surface portion of each of the plurality of electrodes is coplanar with a surface portion of the dielectric layer.

7. The system of claim 6, wherein at least one of the plurality of access transistors is in operable communication with the stimulation circuit and the detection circuit.

8. The system of claim 6, wherein the transistor layer comprises a silicon-on-insulator wafer.

* * * * *